(12) United States Patent
Racenet

(10) Patent No.: US 11,369,401 B2
(45) Date of Patent: *Jun. 28, 2022

(54) REVERSE SEAM RIPPER DISSECTOR

(71) Applicant: Covidien LP, Mansfield, MA (US)

(72) Inventor: Danyel Racenet, Killingworth, CT (US)

(73) Assignee: Covidien LP, Mansfield, MA (US)

( * ) Notice: Subject to any disclaimer, the term of this patent is extended or adjusted under 35 U.S.C. 154(b) by 23 days.

This patent is subject to a terminal disclaimer.

(21) Appl. No.: 15/193,148

(22) Filed: Jun. 27, 2016

(65) Prior Publication Data
US 2016/0302815 A1    Oct. 20, 2016

Related U.S. Application Data

(62) Division of application No. 14/197,418, filed on Mar. 5, 2014, now Pat. No. 9,402,644.

(60) Provisional application No. 61/779,218, filed on Mar. 13, 2013.

(51) Int. Cl.
*A61B 17/32*    (2006.01)
*A61B 17/00*    (2006.01)

(52) U.S. Cl.
CPC ............ *A61B 17/320016* (2013.01); *A61B 2017/00314* (2013.01); *A61B 2017/00327* (2013.01); *A61B 2017/320044* (2013.01)

(58) Field of Classification Search
CPC .. A61B 17/320016; A61B 2017/00314; A61B 2017/320044; A61B 2017/00327
See application file for complete search history.

(56) References Cited

U.S. PATENT DOCUMENTS

| | | | |
|---|---|---|---|
| 2,668,537 A * | 2/1954 | Karla | A61B 17/3201 30/251 |
| 2,865,374 A | 12/1958 | Brown et al. | |
| 3,365,798 A | 1/1968 | Cunningham | |
| 3,600,806 A | 8/1971 | Naccash | |
| 4,729,374 A * | 3/1988 | Alfranca | A61B 17/3201 606/171 |
| 4,986,825 A * | 1/1991 | Bays | A61B 17/1608 600/564 |
| 5,016,353 A | 5/1991 | Iten | |
| 5,089,000 A | 2/1992 | Agee et al. | |
| 5,112,346 A * | 5/1992 | Hiltebrandt | A61B 17/1608 30/251 |

(Continued)

OTHER PUBLICATIONS

Chinese Office Action issued in Chinese Application No. 2014100932843 dated Mar. 23, 2017.
European Search Report from EP 14 15 9093 dated Jun. 17, 2014.

*Primary Examiner* — Jing Rui Ou
(74) *Attorney, Agent, or Firm* — Carter, DeLuca & Farrell LLP

(57) ABSTRACT

A surgical instrument includes an elongate body defining a longitudinal axis, an actuation rod extending through the elongate body and a tool assembly coupled to the elongate body. The tool assembly includes a coupling member coupling the tool assembly to the elongate body and a tool portion pivotally associated with the coupling member. The tool portion includes a projection member including a blunt end portion and a cutting member extending distally outward from the projection member. The tool portion is operatively coupled to the actuation rod. Translation of the actuation rod causes pivotal movement of the tool assembly.

19 Claims, 9 Drawing Sheets

(56) References Cited

U.S. PATENT DOCUMENTS

| | | | |
|---|---|---|---|
| 5,122,152 A | 6/1992 | Mull | |
| 5,312,434 A | 5/1994 | Crainich | |
| 5,395,386 A * | 3/1995 | Slater | A61B 10/06 600/564 |
| 5,397,333 A | 3/1995 | Knoepfler | |
| 5,441,499 A | 8/1995 | Fritzsch | |
| 5,480,408 A | 1/1996 | Chow | |
| 5,792,164 A * | 8/1998 | Lakatos | A61B 17/0218 606/170 |
| 5,899,914 A * | 5/1999 | Zirps | A61B 17/1608 606/170 |
| 7,338,513 B2 | 3/2008 | Lee et al. | |
| 8,336,754 B2 | 12/2012 | Cappola et al. | |
| 9,402,644 B2 | 8/2016 | Racenet | |
| 2002/0069733 A1 | 6/2002 | Allenberg et al. | |
| 2003/0074014 A1 | 4/2003 | Castaneda | |
| 2005/0107667 A1 | 5/2005 | Danitz et al. | |
| 2006/0184187 A1* | 8/2006 | Surti | A61B 17/32002 606/170 |
| 2006/0258954 A1* | 11/2006 | Timberlake | A61B 10/06 600/564 |
| 2006/0276835 A1* | 12/2006 | Uchida | A61B 17/0467 606/205 |
| 2006/0289602 A1* | 12/2006 | Wales | A61B 1/005 227/180.1 |
| 2007/0073301 A1 | 3/2007 | Lieberman | |
| 2007/0156160 A1* | 7/2007 | Petersen | A61B 17/3213 606/167 |
| 2007/0225562 A1* | 9/2007 | Spivey | A61B 17/068 600/121 |
| 2007/0225740 A1 | 9/2007 | Suddaby | |
| 2007/0270895 A1 | 11/2007 | Nobis et al. | |
| 2008/0045989 A1 | 2/2008 | Welborn | |
| 2009/0149868 A1 | 6/2009 | Shelton et al. | |
| 2009/0312773 A1 | 12/2009 | Cabrera et al. | |
| 2010/0076433 A1 | 3/2010 | Taylor et al. | |
| 2010/0298852 A1 | 11/2010 | Slater | |
| 2010/0318119 A1* | 12/2010 | Timberlake | A61B 10/06 606/206 |
| 2012/0150208 A1 | 6/2012 | Messmer | |
| 2012/0197253 A1 | 8/2012 | Nishimura et al. | |
| 2012/0245427 A1 | 9/2012 | Kleyman | |
| 2012/0283520 A1 | 11/2012 | Kleyman | |
| 2013/0012983 A1 | 1/2013 | Kleyman | |
| 2013/0197515 A1* | 8/2013 | Raybin | A61B 18/1492 606/46 |
| 2014/0103093 A1* | 4/2014 | Koch, Jr. | A61B 17/07207 227/180.1 |

* cited by examiner

REVERSE SEAM RIPPER DISSECTOR

CROSS-REFERENCE TO RELATED APPLICATIONS

This application is a divisional of U.S. patent application Ser. No. 14/197,418 filed Mar. 5, 2014, now U.S. Pat. No. 9,402,644, which claims the benefit of and priority to U.S. Provisional Patent Application No. 61/779,218, filed Mar. 13, 2013, the entire disclosure of which is incorporated by reference herein.

BACKGROUND

Technical Field

The present disclosure relates to a surgical instrument, and more particularly, to a surgical instrument for dissecting and cutting tissue.

Background of Related Art

Various surgical procedures are performed in a minimally invasive manner. This includes forming a small opening through a body wall of the patient, e.g., in the abdomen, and inserting only the elongated and small diametered instruments to access the internal body cavities and organs. In general, prior to the introduction of the surgical instruments into the patient's body, insufflation gases are used to enlarge the area surrounding the target surgical site to create a larger, more accessible work area.

Minimally invasive surgery can reduce both trauma to the patient and recovery time for procedures involving small openings. Surgery of this type requires a great deal of skill in manipulating the long narrow endoscopic instruments to a remote site under endoscopic visualization. In addition, due to the relatively small interior dimensions, various surgical instruments need to be switched to perform the required procedure. For examples, dissecting and cutting tissue typically requires a tissue dissector and a surgical knife, respectively, which requires the surgeon to switch instruments during the procedure, which in turn extends the duration of the surgical procedure.

Therefore, there is a need in the art for an improved surgical instrument for dissecting and cutting tissue. More particularly, there is a need for a single surgical instrument that performs the functions of dissecting and cutting tissue.

SUMMARY

In accordance with an embodiment of the present disclosure, there is provided a surgical instrument including an elongate body defining a longitudinal axis, an actuation rod extending through the elongate body and a tool assembly coupled to the elongate body. The tool assembly includes a coupling member coupling the tool assembly to the elongate body and a tool portion pivotally associated with the coupling member. The tool portion includes a projection member including a substantially blunt end portion and a cutting member extending distally outward from the projection member. In particular, the tool portion is operatively coupled to the actuation rod. Translation of the actuation rod causes pivotal movement of the tool portion.

In an embodiment, the cutting member may include a portion in a substantially orthogonal relation with the projection member. In addition, the tool portion may define a gap between the projection member and the cutting member. The gap may be configured and dimensioned to receive tissue therein.

In an embodiment, the surgical instrument may further include a sheath slidably disposed in the coupling member of the tool assembly. In particular, the sheath is movable between a retracted position in which the sheath is disposed entirely in the coupling member and an extended position in which the sheath covers the tool portion. Alternatively, the surgical instrument may include a sheath detachably coupled to the coupling member. The sheath may be configured and dimensioned to enclose and seal the tool portion. In particular, the sheath may be made of a biocompatible fabric including perforations.

In addition, the surgical instrument may further include an articulation neck assembly including a plurality of articulation links pivotally coupled to each other and a pair of articulation cables interconnecting the plurality of articulation links. The articulation neck assembly may interconnect the elongate body and the tool assembly. The articulation neck assembly may further include a rotatable hub defining a helical groove on an outer wall thereof. Proximal ends of the pair of articulation cables may be configured and adapted to slidably engage the helical groove, whereby rotation of the rotatable hub translates the pair of articulation cables in opposite directions.

In an embodiment, the surgical instrument may further include a linkage member pivotally interconnecting the tool portion and the actuation rod. The tool portion may include a torsion spring configured to provide bias toward a neutral position in which the projection member is substantially parallel to the longitudinal axis. A portion of the coupling member of the tool assembly may define a cutout portion configured and dimensioned to receive at least a portion of the tool assembly when the tool portion pivots.

In accordance with an embodiment of the present disclosure, there is provided a surgical instrument including a handle assembly including an actuation knob and a slider, an elongate body defining a longitudinal axis and extending distally from the handle assembly, a tool assembly coupled to the elongate body, a sheath slidably disposed in the tool assembly, an actuation rod extending through the elongate body, and a translation rod operatively interconnecting the sheath with the slider. In particular, the tool assembly includes a coupling member and a tool portion pivotally associated with the coupling member. The tool portion includes a projection member including a blunt end portion and a cutting member connected to the projection member. The sheath is movable between a retracted position in which the sheath is concentrically disposed within the coupling member and an extended position in which the sheath encloses the tool portion. The actuation rod operatively connects the actuation knob with the tool portion. In particular, translation of the actuation rod pivots the tool portion and translation of the translation rod moves the sheath between the retracted and extended positions.

In an embodiment, the cutting member may define an acute angle with respect to the longitudinal axis. The cutting member may be connected to the projection member in an orthogonal relation. The elongate body may define an outer wall and an inner wall. The translation rod may be slidably interposed between the outer wall and the inner wall. The tool assembly may be rotatable about the longitudinal axis.

In an embodiment, the actuation rod may be coupled to a biasing member, whereby the tool portion is biased toward a neutral position in which the projection member is substantially parallel to the longitudinal axis. In addition, the translation rod may be coupled to a biasing member, whereby the sheath is biased toward the retracted position.

BRIEF DESCRIPTION OF THE DRAWINGS

Various embodiments of the present disclosure are described hereinbelow with reference to the drawings, wherein.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

As used herein, the term "distal," as is conventional, will refer to that portion of the instrument, apparatus, device or component thereof which is farther from the user while, the term "proximal," will refer to that portion of the instrument, apparatus, device or component thereof which is closer to the user.

Figure 1:
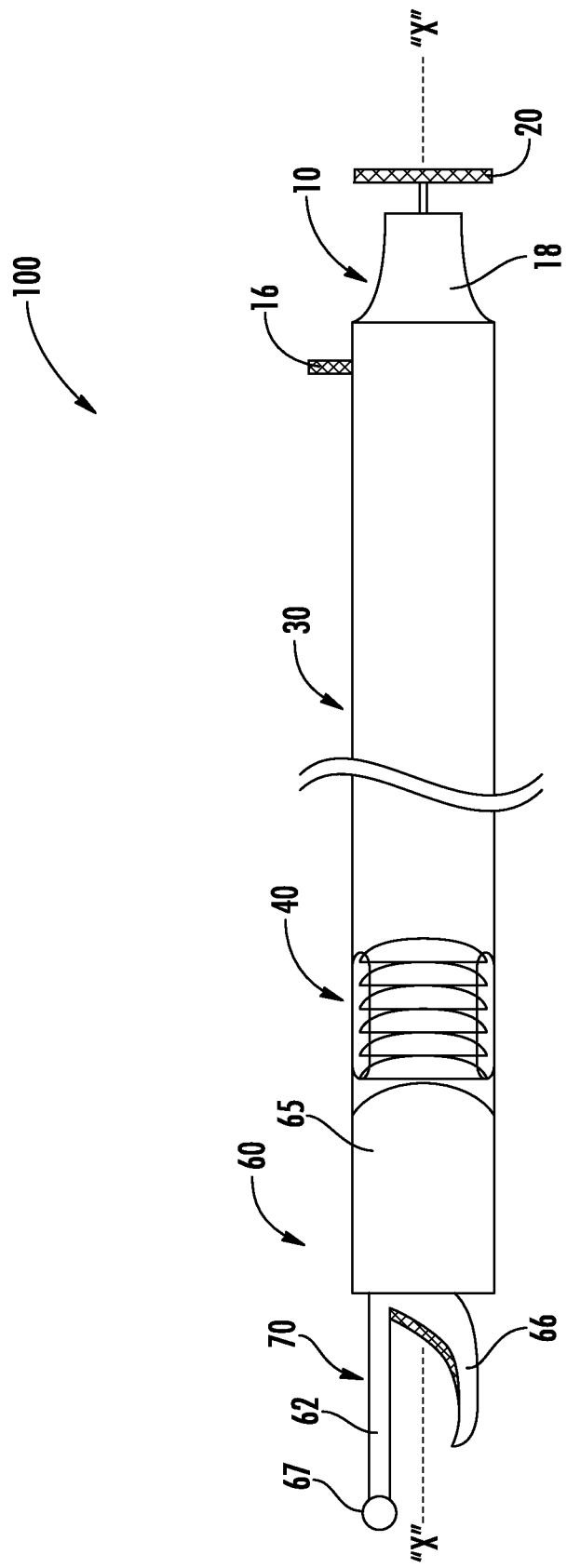
FIG. 1 is a side view of a surgical instrument in accordance with an embodiment of the present disclosure.

With reference to FIG. 1, there is illustrated a surgical instrument 100 for dissecting and cutting tissue and adhesion in accordance with an embodiment of the present disclosure. Surgical instrument 100 includes a handle assembly 10, an elongate body 30 extending distally from handle assembly 10, an articulation neck assembly 40 secured to a distal portion of elongate body 30 and a tool assembly 60 operatively coupled to handle assembly 10 and extending distally from articulation neck assembly 40. Tool assembly 60 includes a coupling member 65 and a tool portion 70 including a substantially blunt dissector 62 configured and adapted to dissect tissue and a cutting member 66 configured to cut tissue or adhesion, as will be described in detail below.

Figure 2:
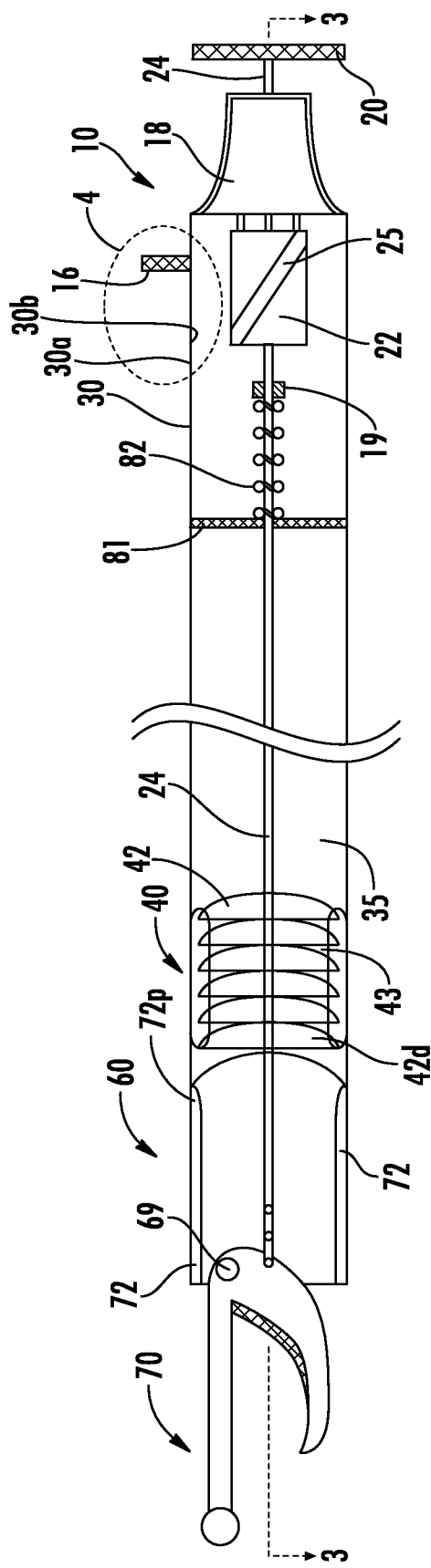
FIG. 2 is a longitudinal cross-sectional view of the surgical instrument of FIG. 1.
Figure 3:
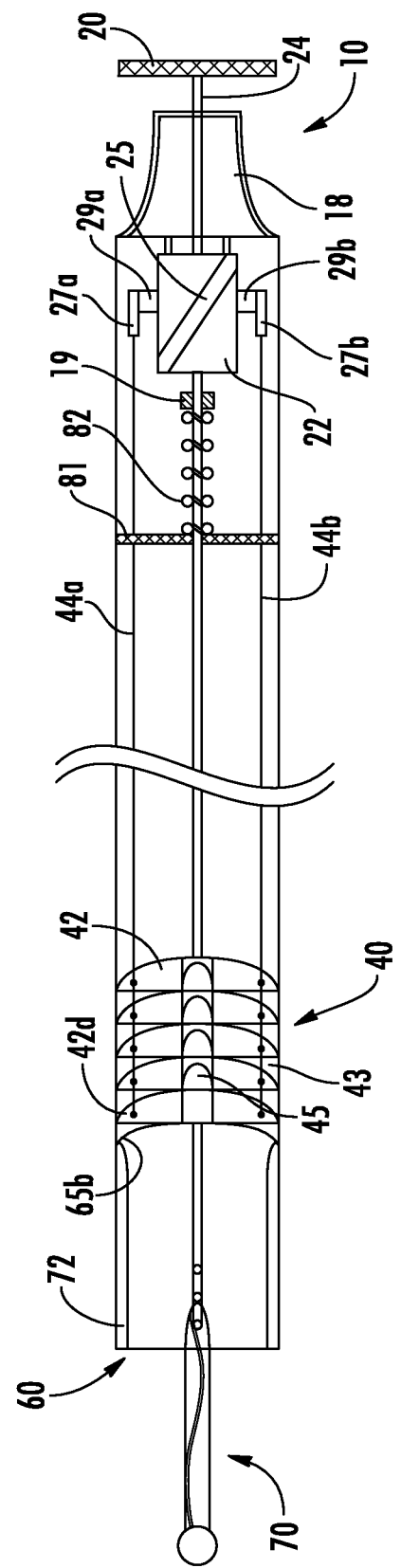
FIG. 3 is a cross-sectional view taken along section line 3-3 in FIG. 2.
Figure 7:
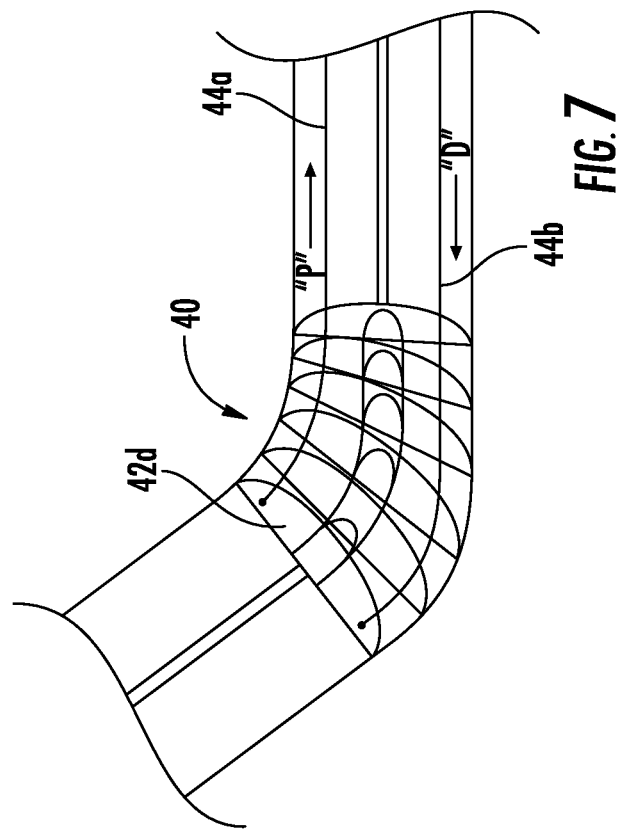
FIG. 7 is a partial cross-sectional view of an articulation neck assembly of the surgical instrument of FIG. 1 when the articulation knob is rotated.

With reference now to FIGS. 2 and 3, handle assembly 10 includes a slider 16, an articulation knob 18 and an actuation knob 20. Slider 16 is operatively coupled with a sheath 72 configured and dimensioned to cover tool portion 70 of tool assembly 60 when tool portion 70 is not in use (FIG. 5), as will be discussed in detail below. Articulation knob 18 may be rotated to provide articulation of articulation neck assembly 40 to enable, for example, a side-to-side, movement of tool assembly 60 (FIG. 7). Actuation knob 20 may be moved distally to pivot tool assembly 60 (FIG. 13), as will be described in detail below. Additionally, actuation knob 20 may be rotated about a longitudinal axis "X-X" (FIG. 1) of the surgical instrument 100 to selectively position tool assembly 60 to any rotational orientation about longitudinal axis "X-X.".

Figure 4:
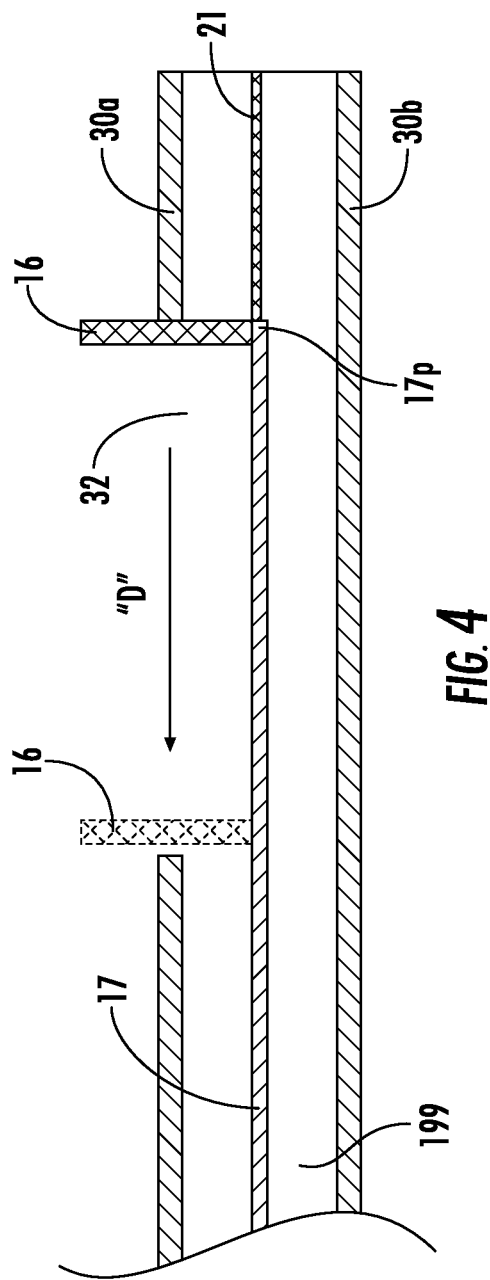
FIG. 4 is a cross-sectional view of the area of detail indicated in FIG. 2.
Figure 5:
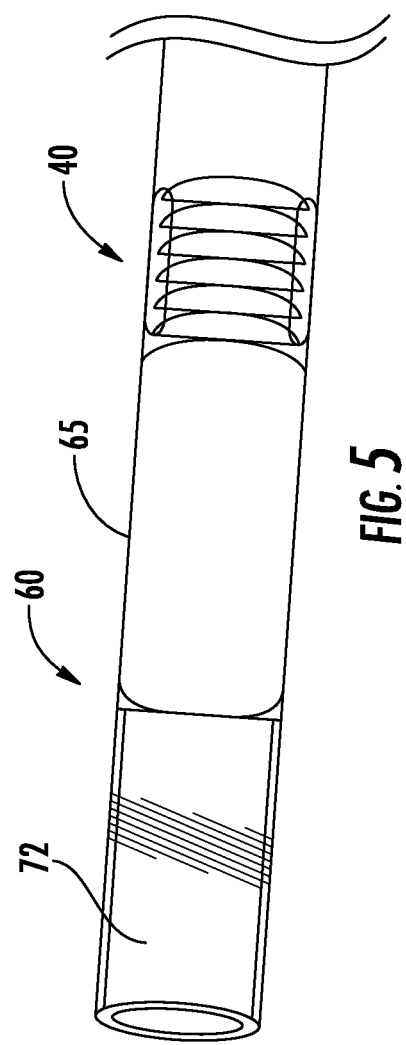
FIG. 5 is a partial perspective view of a tool assembly of the surgical instrument of FIG. 1 illustrating a sheath in an extended position.
Figure 8:
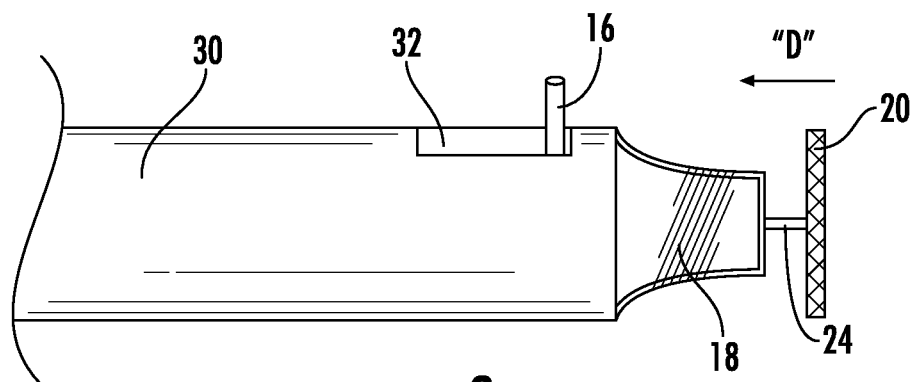
FIG. 8 is a partial perspective view of the surgical instrument of FIG. 1 illustrating an actuation knob in a neutral position.

With reference now to FIGS. 2-5, slider 16 is operatively coupled with a sheath 72 movable between a retracted position in which the entire sheath 72 is concentrically positioned in coupling member 65 adjacent articulation neck assembly 40 (FIG. 2) and an extended position in which sheath 72 covers tool portion 70 entirely when tool portion 70 is not in use (FIG. 5). In this manner, inadvertent contact of tool portion 70 with tissue during, for example, insertion and removal of surgical instrument 100, into and from the patient may be avoided. Slider 16 is slidably disposed in a slot 32 (FIGS. 4 and 8) defined in elongate body 30. In particular, slider 16 is operatively attached to translation rod 17 that is coupled to sheath 72. Translation rod 17 extends through elongate body 30 and at least partially into coupling member 65 of tool assembly 60.

With particular reference to FIGS. 2 and 4, elongate body 30 defines an annular space 199 (FIG. 4) between inner and outer walls 30a, 30b. Translation rod 17 is slidably placed in annular space 199 between outer wall 30a and inner wall 30b of elongate body 30, whereby translation of slider 16 in the direction of arrow "D" (FIG. 4) by the surgeon causes concomitant translation of translation rod 17 in space 199, which in turn places sheath 72 in the extended position. In particular, translation rod 17 conforms to the contour or curvature of annular space 199 of elongate body 30 to reduce the thickness of elongate body 30 and to facilitate sliding movement of translation rod 17 between outer and inner walls 30a, 30b of elongate body 30. Alternatively, translation rod 17 may be a tubular member slidably disposed between inner and outer walls 30a, 30b of elongate body 30. Such configuration may provide a more secure connection with and control of sheath 72.

Additionally, slider 16 is operatively coupled with a biasing member 21 such as an elastic band anchored to a proximal portion of elongate body 30. Under such configuration, sheath 72 is biased toward the retracted position, whereby the surgeon can slide slider 16 in the direction of arrow "D" to cover tool portion 70 when needed. When slider 16 is moved to the distal-most position (as shown in phantom in FIG. 4), sheath 72 is positioned in the extended position (FIG. 5).

With particular reference to FIG. 5, sheath 72 is a cylindrically shaped member slidably supported in coupling member 65 of tool assembly 60. Sheath 72 slidably and concentrically engages inner wall 65b (FIG. 3) of coupling member 65. Sheath 72 defines a channel configured and dimensioned to receive tool portion 70 including a blunt dissector 62 and a cutting member 66 therethrough. While sheath 72 is movable between the fully retracted and fully extended positions, it is also envisioned that sheath 72 may partially cover tool portion 70, such that the surgeon may utilize blunt dissector 62 while cutting member 66 is covered by sheath 72. It is contemplated that a locking mechanism (not shown) may be added to slider 16 to lock sheath 72 at a desired longitudinal position with respect to tool portion 70.

Figure 6:
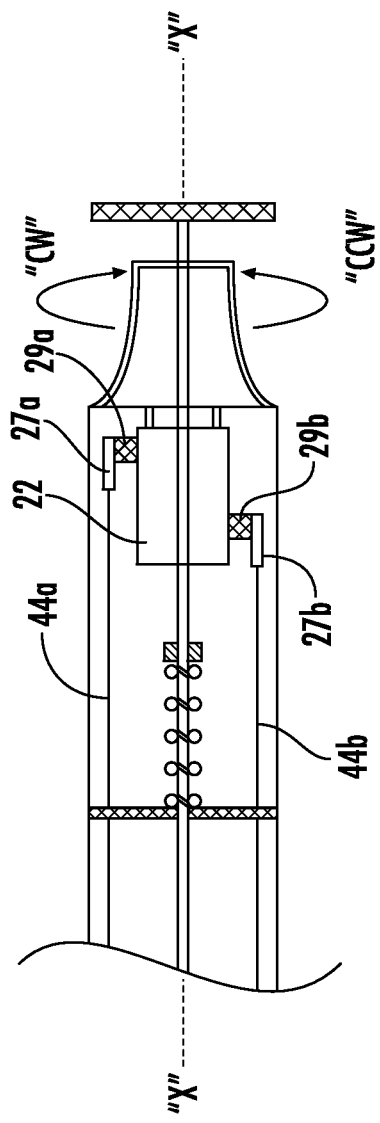
FIG. 6 is a partial cross-sectional view of a handle assembly of the surgical instrument of FIG. 1 illustrating rotation of an articulation knob.

With reference back to FIGS. 2 and 3, handle assembly 10 further includes articulation knob 18 to enable, for example, a side-to-side, movement of tool assembly 60 at articulation neck assembly 40. Articulation knob 18 is rotatably secured to a distal end of elongate body 30. In particular, articulation knob 18 is rotatably coupled with a rotatable hub 22 rotatably disposed within elongate body 30 for concomitant rotation therewith. Rotatable hub 22 defines a helical groove 25 on an outer surface of thereof. Rotatable hub 22 further includes a pair of arms 27a, 27b (FIG. 3) each having a respective finger 29a, 29b. Each finger 29a, 29b is configured and adapted to slidably engage helical groove 25 of rotatable hub 22. A distal end of each arm 27a, 27b is coupled with respective articulation cable 44a, 44b (FIG. 3). When articulation neck assembly 40 is in a neutral position, as shown in FIG. 3, articulation neck assembly 40 is aligned with a longitudinal axis "X-X" (FIG. 1) of surgical instrument 100, and fingers 29a, 29b are aligned at a longitudinal position. However, upon rotation of articulation knob 18 about longitudinal axis "X-X," in either direction "CW," "COW" (FIG. 6), fingers 29a, 29b travel in opposite longitudinal directions along helical groove 25 of rotatable hub 22. In this manner, one of arms 27a, 27b pulls the respective articulation cable 44a, 44b proximally and the other arm 27a, 27b is pulled by the other articulation cable 44a, 44b distally. The simultaneous translation of articulation cables 44a, 44b in opposite directions "P," "D" (FIG. 7) enables articulation of articulation neck assembly 40, which in turn provides a side-to-side movement of tool assembly 60, as will be described in detail hereinbelow. While articulations cables 44a, 44b are two separate cables 44a, 44b, independently attached to distal-most link 42d, it is also envisioned that articulation cables 44a, 44b can be a single cable connected through distal-most link 42d. It is also envisioned that articulation knob 18 enables rotational movement of tool assembly 60.

With reference back to FIG. 3, handle assembly 10 includes actuation knob 20 operatively connected to an actuation rod 24. Actuation rod 24 extends through the entire length of elongate body 30 and is operatively coupled to tool assembly 60. Actuation rod 24 is configured and dimensioned to extend through articulation knob 18 and rotatable hub 22. In particular, actuation rod 24 may be relatively flexible to accommodate articulation of articulation neck assembly 40. Flexibility may be achieved in any number of ways. For example, actuation rod 24 may be comprised of a flexible material, may include segments and/or may have material removed from it, such as grooves, to increase flexibility.

Figure 9:
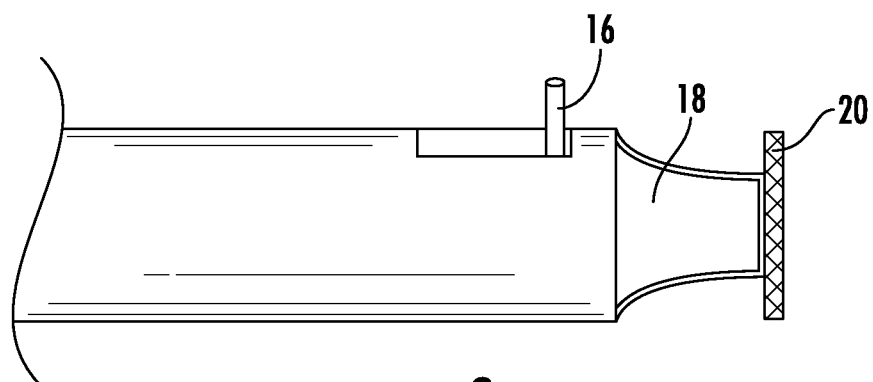
FIG. 9 is a partial perspective view of the surgical instrument of FIG. 8 illustrating actuation of the actuation knob.
Figure 10:
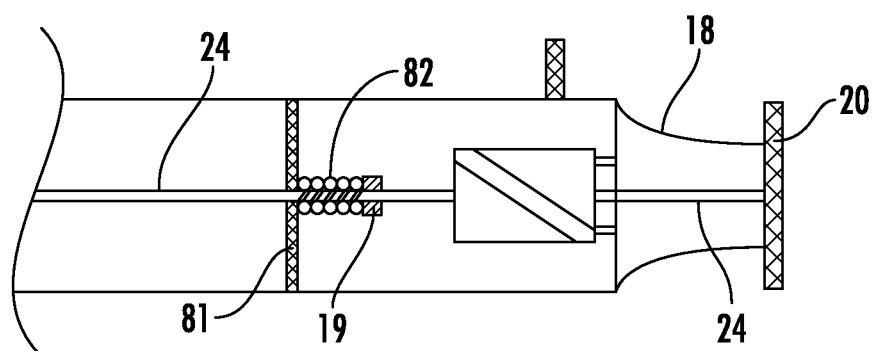
FIG. 10 is a partial cross-sectional view of the surgical instrument of FIG. 9 illustrating actuation of the actuation knob.

With continued reference to FIG. 3, actuation rod 24 extends through elongate body 30 and at least partially into tool assembly 60. Elongate body 30 includes an anchor wall 81 extending radially inward and defining a bore configured and dimensioned to receive actuation rod 24 therethrough. Actuation rod 24 further includes a stopper 19 fixedly attached to actuation rod 24 and translates with actuation rod 24 as a unitary construct. Stopper 19 is configured and adapted to secure a biasing member 82 thereto. Under such configuration, biasing member 82 is positioned between stopper 19 and anchor wall 81 of elongate body 30. The bore defined in anchor wall 81 is dimensioned to only receive actuation rod 24 therethrough. In this manner, when actuation knob 20 is moved in the direction of arrow "D" (FIG. 8), actuation rod 24 is translated distally (FIG. 9), and thereby compressing biasing member 82 (FIG. 10) between stopper 19 and anchor wall 81. Translating actuation rod 24 pivots tool portion 70 of tool assembly 60 about pivot 69 (FIG. 2), as will be discussed in detail hereinbelow. Under such configuration, tool assembly 60 is biased toward a neutral position (FIGS. 1 and 2), whereby release of actuation knob 20 allows biasing member 82 to expand and urges stopper 19 proximally, which moves actuation rod 24 proximally and positions tool portion 70 of tool assembly 60 in the neutral position. It is also contemplated that a locking mechanism (not shown) may be added to handle assembly 10 to lock tool portion 70 in a desired rotated position. Reference may be made to U.S. Pat. No. 8,336,754, filed on Feb. 4, 2011, and U.S. Patent Application Publication No. 2013/0012983, filed on Jul. 9, 2012, the entire contents of each of which are incorporated herein by reference, for a detailed discussion of the construction and operation of a locking mechanism.

Figure 13:
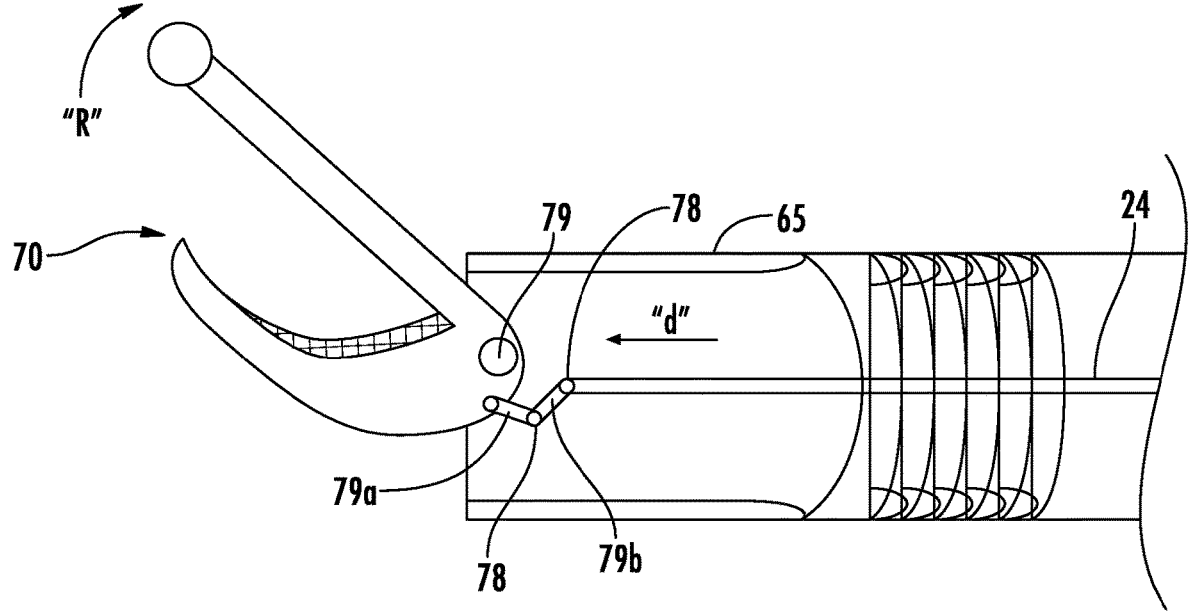
FIG. 13 is a partial cross-sectional view of the surgical instrument of FIG. 1 illustrating pivotal movement of the tool portion of the tool assembly.

With reference now to FIGS. 1 and 8-10, when actuation knob 20 is in a neutral position (FIG. 8), blunt dissector 62 of tool assembly 60 is substantially parallel to the longitudinal axis "X-X." However, when actuation knob 20 is moved distally (FIG. 9) tool portion 70 pivots against the bias of biasing member 82 (FIG. 13). Release of actuation knob 20 urges tool portion 70 back in the neutral position in which blunt dissector 62 is substantially parallel to the longitudinal axis "X-X."

With reference back to FIGS. 2 and 3, elongate body 30 defines a working channel 35 dimensioned and configured to accommodate rotatable hub 22, actuation rod 24, and articulation cable 44a, 44b, as described hereinabove. While elongate body 30, as shown, is substantially straight, it is also contemplated that elongate body 30 may be relatively flexible to facilitate insertion into a patient's body. A distal portion of elongate body 30 is coupled with articulation neck assembly 40. Articulation neck assembly 40 includes a plurality of articulation links 42. Each articulation link 42 is pivotally associated with at least one adjacent articulation link 42. In addition, each articulation link 42 has a semispherical shape, which defines a gap 43 between adjacent articulation links 42. Such gap 43 enables pivotal movement of each link 42. In addition, each link 42 defines a bore on each opposing side of link 42 with respect to pivot axis 45 (FIG. 3). Each bore is configured and dimensioned to receive respective articulation cable 44a, 44b, therethrough. In particular, distal-most link 42d is securely connected to articulation cables 44a, 44b. In this manner, translation of articulation cables 44a, 44b in opposite directions enables articulation movement of neck assembly 40, thereby enabling, for example, a side-to-side, movement of tool assembly 60 (FIG. 7).

Figure 11:
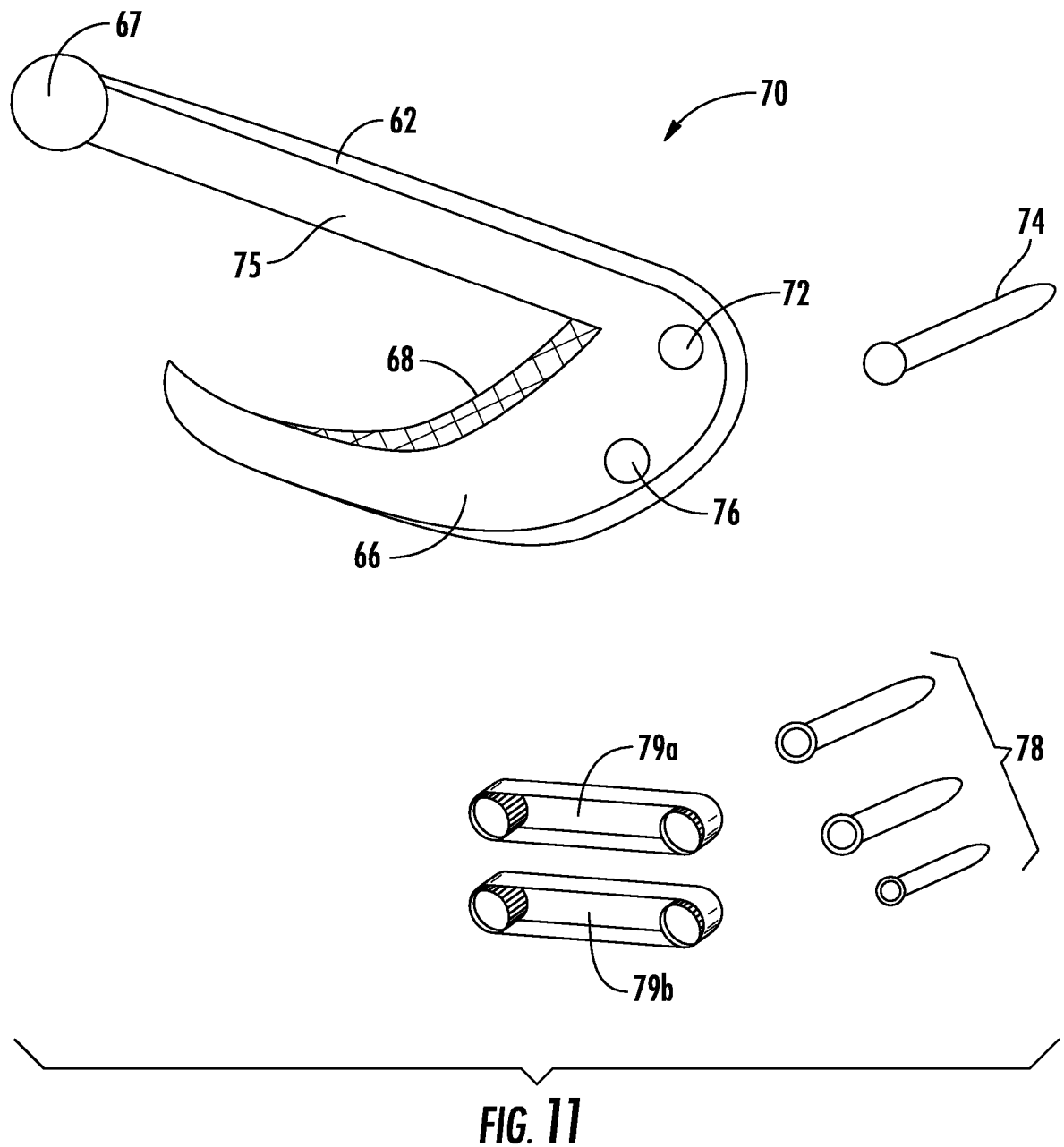
FIG. 11 is an exploded perspective view of a tool portion of a tool assembly of the surgical instrument of FIG. 1 with parts separated.

With reference now to FIGS. 1 and 11, tool assembly 60 is operatively coupled to handle assembly 10 and extends distally from articulation neck assembly 40. Tool assembly 60 includes a tool portion 70 and coupling member 65. Tool portion 70 includes a blunt dissector 62 having a projection member 75 and a blunt end portion 67 at a distal end thereof. Blunt end portion 67 is configured and adapted to dissect tissue, and projection member 75 is longitudinally tapered to facilitate dissection of tissue, as well as insertion into the body cavity. Blunt dissector 62 may be substantially blunt in that it may have an end with squared-off edges, at least one slightly rounded edge or a slightly rounded tip. Cutting member 66 extends distally outward from projection member 75. In particular, cutting member 66 may define a substantially L-shaped member. Alternatively, cutting member 66 may define a curved or straight shape. Cutting member 66 and blunt dissector 62 may be formed monolithically or integrally. Cutting member 66 may be positioned above, below, or to either side of blunt dissector 62. Cutting member 66 includes a knife blade 68 configured and adapted to cut tissue and adhesion. Knife blade 68 extends from a portion of cutting member 66 adjacent blunt dissector 62 to a portion of cutting member 66 substantially parallel to blunt dissector 62. In order to facilitate cutting of tissue and adhesion, knife blade 68 may define an acute angle with respect to blunt dissector 62. Alternatively, knife blade 68 may define an arcuate portion (not shown) to facilitate cutting of tissue.

Figure 12:
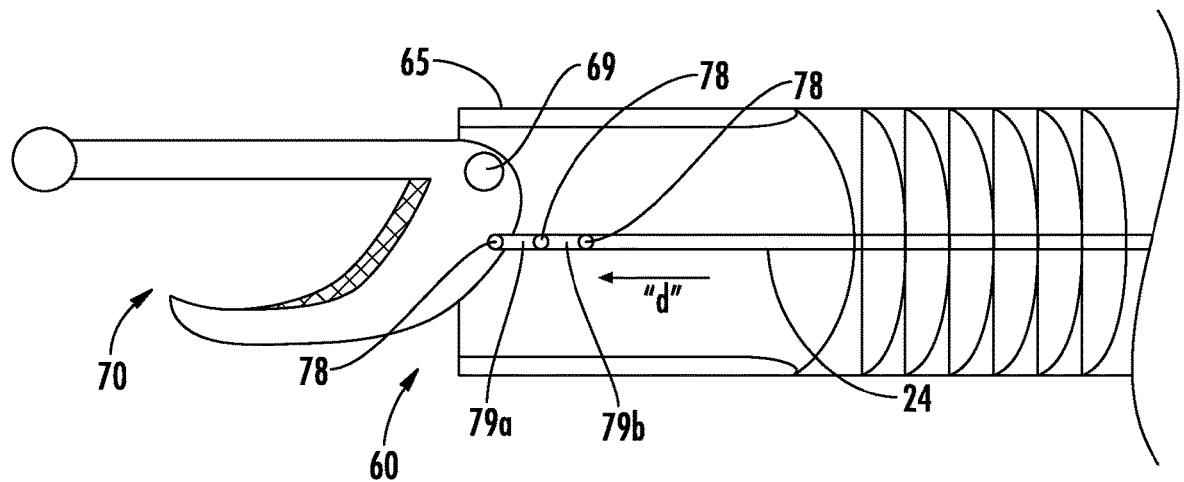
FIG. 12 is a partial cross-sectional view of the surgical instrument of FIG. 1 when the tool assembly is in a neutral position.

With particular reference to FIGS. 11-13, tool portion 70 defines a pivot bore 72 configured and dimensioned to receive pivot pin 74 to pivotally secure tool portion 70 to coupling member 65. In addition, tool portion 70 further defines an actuation linkage bore 76 configured and dimensioned to receive a linkage pin 78. Tool portion 70 is coupled to actuation rod 24 through a pair of pivotally connected linkage members 79a, 79b. Linkage members 79a, 79b are pivotally connected by linkage pins 78.

With particular reference to FIGS. 12 and 13, tool portion 70 is pivotally connected to coupling member 65 and operatively coupled to actuation rod 24 through linkage members 79a, 79b. Under such configuration, as actuation knob 20 is moved distally, actuation rod 24 is translated distally in the direction of arrow "D." Actuation rod 24 pushes pivotally connected linkage members 79a, 79b distally, which results in pivotal movement of tool assembly 60 in the direction of "R" about pivot point 69.

Actuation knob 20 can be moved for pivotal movement of tool portion 70 in the direction of arrow "R." However, it is also envisioned that actuation rod 24 may be modified such that when an actuation knob is moved distally, tool portion 70 rotates in the direction of arrow "R," but when the actuation knob is moved proximally, tool portion 70 rotates in the direction opposite of arrow "R."

In use, the surgeon creates an incision for example, in the abdomen, of a patient. A portal, known to those skilled in the art, may optionally be inserted into the incision to prevent the incision from closing. Reference may be made to U.S. Patent Application Publication Nos. 2012/0245427, filed on Feb. 10, 2012, and 2012/0283520, filed on Apr. 5, 2012, the entire contents of each of which are incorporated herein by reference, for a detailed discussion of the construction and operation of a portal. Surgical instrument 100 with sheath 72 in the extended position is inserted into the body cavity of the patient. After surgical instrument 100 is positioned in the body cavity, the surgeon may then manipulate handle assembly 100 to orient tool assembly 60 toward the target site. Through articulation of neck assembly 40 and rotation of tool assembly 60, tool assembly 60 can be properly positioned adjacent the target site.

After surgical instrument 100 has been properly positioned adjacent the surgical site, the surgeon may partially retract sheath 72 to expose blunt dissector 62 to the surgical site. The surgeon can use blunt end portion 67 to dissect the desire tissue. Thereafter, the surgeon may retract sheath 72 entirely (if needed) such that the entire tool portion 70 is exposed to the surgical site. The surgeon can then use cutting member 66 to cut tissue and/or adhesion. Upon completion of dissection and/or cutting of tissue, the surgeon can place sheath 72 in the extended position to cover tool portion 70. Thereafter, the surgeon may remove surgical instrument 100 from the surgical site.

Figure 14:
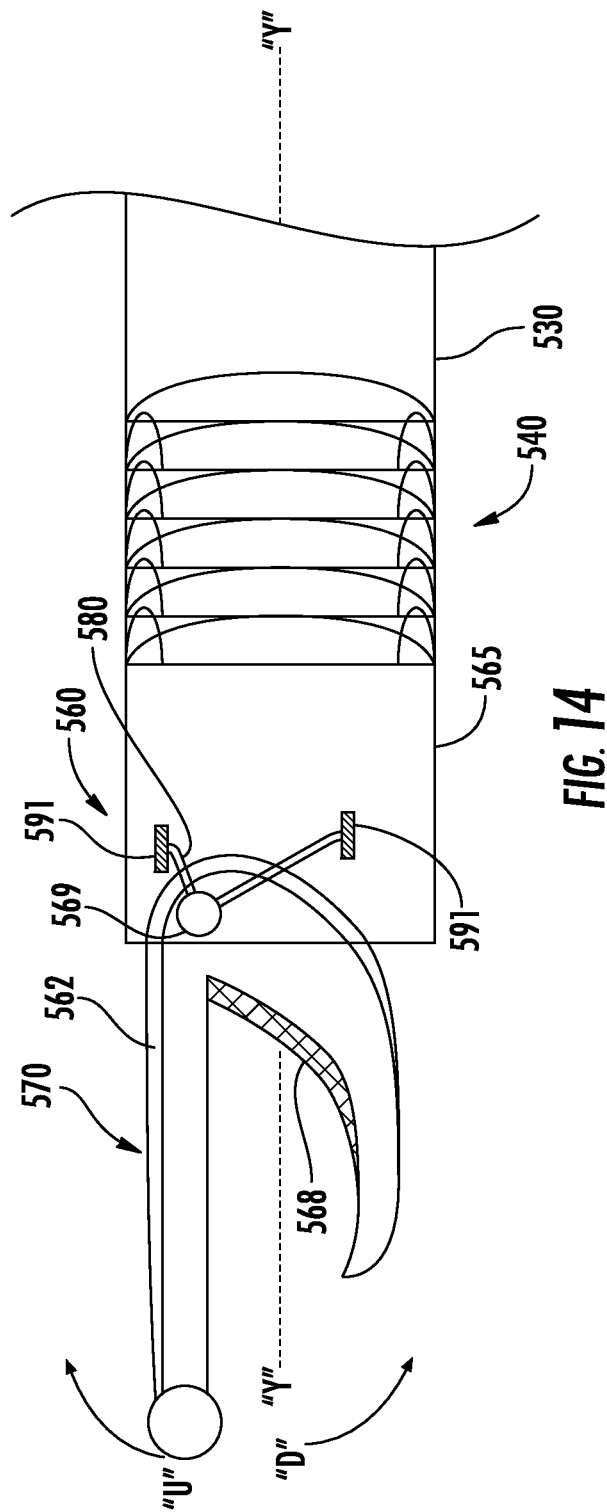
FIG. 14 is a partial cross-sectional view of a surgical instrument in accordance with an embodiment of the present disclosure.

With reference now to FIG. 14, there is shown a tool assembly 560 in accordance with another embodiment of the present disclosure. In contrast to tool assembly 60, tool assembly 560 utilizes a torsion spring 580. However, other parts of tool assembly 560 are substantially identical to tool assembly 60 and will not be discussed herein. Torsion spring 580 is securely anchored to supports 591 provided on an inner wall of coupling member 565 of tool assembly 560. Tool assembly 560 is biased toward a neutral position in which a blunt dissector 562 is substantially parallel to a longitudinal axis "Y-Y" defined by an elongate body 530. Alternatively, tool assembly 560 is biased toward a neutral position in which a knife blade 568 is substantially orthogonal to the longitudinal axis "Y-Y." However, supports 591 may be positioned such that blunt dissector 562 defines a more desirable angle with respect to the longitudinal axis "Y-Y" in the neutral position. Torsion spring 580 enables tool assembly 560 to rotatably adjust the angle of blunt dissector 562 with respect to the longitudinal axis "Y-Y" based on the thickness and/or contour of tissue or adhesion. Tool assembly 560 may rotate in the direction of either "U" or "D" based on the thickness or contour of tissue or adhesion. The rotatably adjustable characteristic of tool assembly 560 further reduces trauma to the cutting surface of tissue or adhesion. Moreover, such configuration may simplify the configuration of the surgical instrument by eliminating various parts of the surgical instrument such as, for example, actuation knob 20 and linkage members 79a, 79b, and thereby lowering the manufacturing costs.

Figure 15:
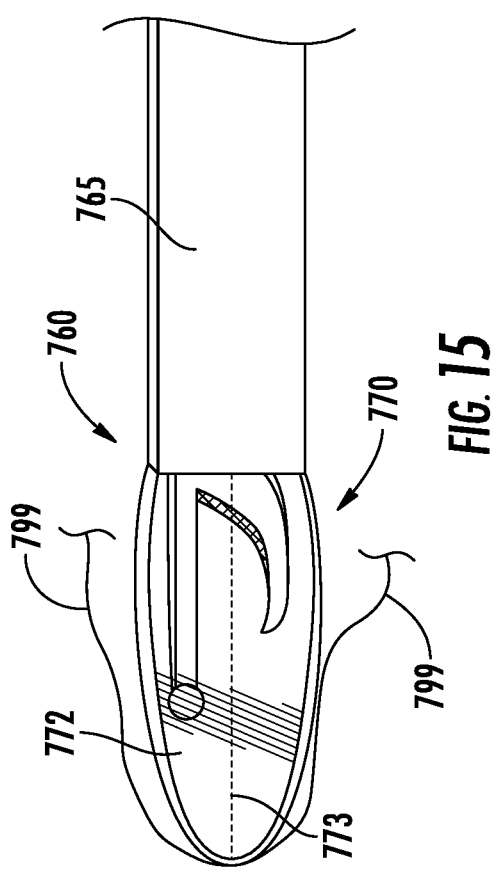
FIG. 15 is a partial perspective view of a surgical instrument in accordance with an embodiment of the present disclosure.

With reference now to FIG. 15, it is further contemplated that a tool assembly 760 may include a removable sheath 772 that is made of, for example, biocompatible fabric. Tool assembly 760 is sterilized and packaged with sheath 772 covering the entire tool portion 770. Sheath 772 includes a perforated portion or break 773 for easy tearing or detachment by the surgeon. In particular, sheath 772 includes a plurality of strings 799 attached to various points on a distal portion of sheath 772 such that when the surgeon pulls strings 799 remotely, sheath 772 tears along break 773 and detaches from coupling member 765, and thereby exposing tool portion 770. The removal of sheath 772 can be done once tool assembly 760 has been placed near the desired surgical site. Sheath 772 can be attached to coupling member 765 by, for example, a biocompatible adhesive.

Figure 17:
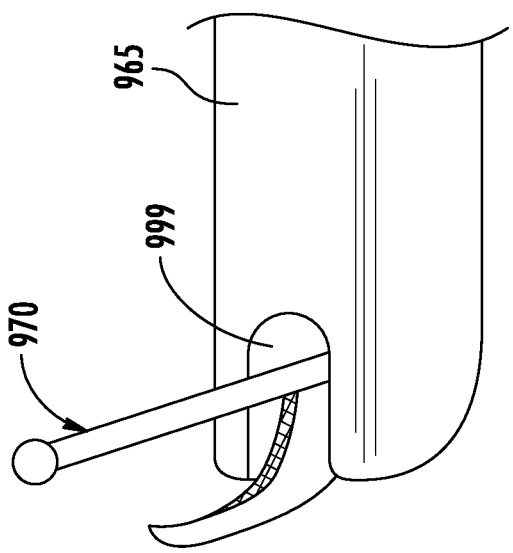
FIG. 17 is a partial perspective view of the surgical instrument of FIG. 16 illustrating pivotal movement of the tool portion of the tool assembly.
Figure 16:
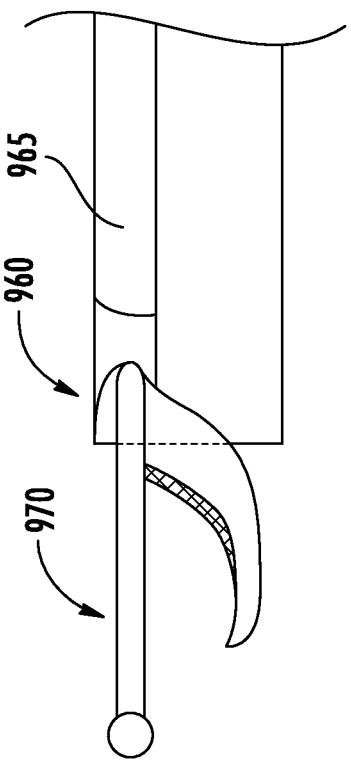
FIG. 16 is a partial perspective view of a surgical instrument in accordance with an embodiment of the present disclosure illustrating a tool portion of a tool assembly in a neutral position.

With reference to FIGS. 16 and 17, it is further contemplated that a tool assembly 960 in accordance with another embodiment of the present disclosure, includes a tool portion 970 and a coupling member 965. Tool portion 970 is substantially identical to tool portions 70, 570. However, coupling member 965 defines a cutout portion 999 such that tool portion 970 pivotally associated with coupling member 965 has a greater degree of rotational freedom with respect to coupling member 965. By providing a greater degree of rotational freedom, the surgeon can better manipulate tool portion 970, which may reduce trauma to the patient and shorten the duration of surgical procedure.

Although the illustrative embodiments of the present disclosure have been described herein with reference to the accompanying drawings, the above description, disclosure, and figures should not be construed as limiting, but merely as exemplifications of particular embodiments. Persons skilled in the art will understand that the devices and methods specifically described herein and illustrated in the accompanying drawings are non-limiting exemplary embodiments. For example, one skilled in the art may contemplate utilizing surgical instrument 100 in an open surgery. It is to be understood, therefore, that the disclosure is not limited to those precise embodiments, and that various other changes and modifications may be effected therein by one skilled in the art without departing from the scope or spirit of the disclosure.

The invention claimed is:

1. A surgical instrument comprising:
an elongate body defining a longitudinal axis; and
a tool assembly coupled to the elongate body, the tool assembly including:
 a coupling member including a free distal end and coupled to the elongate body; and
 a tool portion pivotally secured with the coupling member by a pivot pin about a pivot fixed to the coupling member, the tool portion including:
  a projection member including a blunt end portion distal of the coupling member; and
  a cutting member including a blade and extending outward from the projection member such that the projection member and the cutting member define a gap therebetween, the blade having a curvature extending from the projection member to a portion of the cutting member that is substantially parallel to the projection member the cutting member distal of the pivot pin, wherein the tool portion is pivotable between a first position in which the projection member is substantially aligned with the longitudinal axis of the elongate body such that the blunt end portion of the projection member is a distal-most portion of the surgical instrument and opposing lateral surfaces of the blunt end portion are exposed for direct contact with tissue, and a second position in which the projection member is offset from the longitudinal axis, wherein the blade of the cutting member is distal of the free distal end of the coupling member when the tool portion is in the first position.

2. The surgical instrument according to claim 1, wherein the tool portion is biased toward the first position.

3. The surgical instrument according to claim 1, wherein the tool portion is integrally formed as a single construct.

4. The surgical instrument according to claim 1, further comprising an actuation rod coupled to the tool portion of the tool assembly such that translation of the actuation rod transitions the tool portion between the first and second positions.

5. The surgical instrument according to claim 4, further comprising a linkage member pivotally interconnecting the tool portion and the actuation rod.

6. The surgical instrument according to claim 4, further comprising an articulation neck assembly interconnecting the elongate body and the tool assembly, the articulation neck assembly including a plurality of articulation links pivotally coupled to each other and a pair of articulation cables interconnecting the plurality of articulation links.

7. The surgical instrument according to claim 6, wherein the articulation neck assembly further includes a rotatable hub defining a helical groove on an outer wall thereof, wherein proximal ends of the respective articulation cables are configured to slidably engage the helical groove, whereby rotation of the rotatable hub translates the respective articulation cables in opposite directions.

8. A surgical instrument comprising:
an elongate body defining a longitudinal axis; and
a tool assembly coupled to the elongate body, the tool assembly including:
 a coupling member including a free distal end; and
 a tool portion pivotally secured with the coupling member by a pivot pin fixedly secured with the coupling member, the tool portion including:
  a projection member including a blunt end portion distal of the coupling member; and
  a cutting member including a blade and distal of the pivot pin, the projection member and the cutting member defining a fixed gap therebetween, the blade having a curvature extending from the projection member to a portion of the cutting member that is substantially parallel to the projection member, the tool portion transitionable between a first orientation in which the projection member defines a first angle with respect to the longitudinal axis of the elongate body and a second orientation in which the projection member defines a second angle with respect to the longitudinal axis, wherein a portion of the projection member is distal of the cutting member, and wherein the blunt end portion of the projection member is a distal-most portion of the surgical instrument such that laterally opposing surfaces of the blunt end portion are exposed for direct contact with tissue when the tool portion is in one of the first and second orientations, wherein the blade of the cutting member is distal of the free distal end of the coupling member when the projection member is substantially aligned with the longitudinal axis of the elongate body.

9. The surgical instrument according to claim 8, wherein at least a portion of the cutting member defines an acute angle with respect to the projection member.

10. The surgical instrument according to claim 8, wherein the projection member of the tool portion is substantially aligned with the longitudinal axis of the elongate body when the tool portion is in the first orientation.

11. The surgical instrument according to claim 8, wherein the tool portion is biased toward the first orientation.

12. The surgical instrument according to claim 8, wherein the tool assembly is rotatable about the longitudinal axis of the elongate body.

13. The surgical instrument according to claim 8, further comprising an articulation neck assembly interconnecting the elongate body and the tool assembly, the articulation neck assembly including a plurality of articulation links pivotally coupled to each other and a pair of articulation cables interconnecting the plurality of articulation links.

14. The surgical instrument according to claim 13, wherein the articulation neck assembly further includes a rotatable hub defining a helical groove on an outer wall thereof, wherein proximal ends of the respective articulation cables are configured to slidably engage the helical groove, whereby rotation of the rotatable hub translates the respective articulation cables in opposite directions.

15. A surgical instrument comprising:
   a tool assembly including:
      a coupling member including a free distal end; and
      a tool portion pivotally secured with the coupling member by a pivot pin about a pivot fixed to the coupling member, the tool portion including:
         a projection member including a blunt end portion distal of the coupling member; and
         a cutting member including a blade and extending outward from a proximal portion of the projection member such that the projection member and the cutting member define a gap therebetween, the gap distal of the pivot, the blade having a curvature extending from the projection member to a portion of the cutting member that is substantially parallel to the projection member, wherein the tool portion is transitionable between a first position in which the projection member is substantially aligned with a longitudinal axis of the surgical instrument such that the blunt end portion of the projection member is a distal-most portion of the surgical instrument and diametrically opposing surfaces of the blunt end portion are exposed for direct contact with tissue, and a second position in which the projection member is offset from the longitudinal axis, wherein the blade of the cutting member is distal of the free distal end of the coupling member when the tool portion is in the first position.

16. The surgical instrument according to claim 15, wherein the tool portion is biased towards the first position.

17. The surgical instrument according to claim 15, wherein the tool portion is integrally formed as a single construct.

18. The surgical instrument according to claim 15, further comprising an actuation rod coupled to the tool portion such that translation of the actuation rod transitions the tool portion between the first and second positions.

19. The surgical instrument according to claim 18, further comprising a linkage member pivotally interconnecting the tool portion and the actuation rod.

\* \* \* \* \*